United States Patent [19]

Suthanthiran et al.

[11] Patent Number: 4,994,013
[45] Date of Patent: Feb. 19, 1991

[54] PELLET FOR A RADIOACTIVE SEED

[75] Inventors: Krishnan Suthanthiran, Lorton, Va.; Raj Lakshman, Bethesda, Md.

[73] Assignee: Best Industries, Inc., Springfield, Va.

[21] Appl. No.: 225,302

[22] Filed: Jul. 28, 1988

[51] Int. Cl.⁵ ............................................. A61N 5/10
[52] U.S. Cl. .................................................. 600/008
[58] Field of Search ............................. 600/1, 3, 7, 8; 424/1.1; 427/5, 6

[56] References Cited

U.S. PATENT DOCUMENTS

| | | | |
|---|---|---|---|
| 821,655 | 5/1906 | Lieber | 600/1 |
| 1,603,767 | 10/1926 | Harris | 600/3 |
| 2,269,458 | 1/1942 | Kahn . | |
| 3,334,050 | 8/1967 | Grotenhuis . | |
| 3,351,049 | 11/1967 | Lawrence . | |
| 4,228,146 | 10/1980 | Imamura . | |
| 4,323,055 | 4/1982 | Kubiatowicz . | |
| 4,702,228 | 10/1987 | Russell et al. | 600/8 |

OTHER PUBLICATIONS

"Carbon Black", Webster's New World Dic., 2nd College Ed., World Publ. Co., New York, 1970, p. 213.
Encyclopedia of Polymer Science and Technology, vol. 3, John Wiley and Sons, New York, 1965, pp. 367 and 399.
"Ammarium Phosphomolybdate", Merck Index, 9th Ed. Merck and Co., Inc., Rahway, NJ 1976, p. 585.
Technical Innovations and Notes, "Physical Dosimetry of I seeds of a New Design for Interstitial Implant", vol. 9, pp. 1747-1752.

*Primary Examiner*—William E. Kamm
*Assistant Examiner*—John Hanley
*Attorney, Agent, or Firm*—Parkhurst, Wendel & Rossi

[57] ABSTRACT

A pellet for a radioactive seed, suitable for use in certain medical radiological treatments, comprising a metallic X-ray detectable marker rod such as tungsten coated with a radioactive-absorbing material such as carbon in a binder wherein a radioactive material is absorbed. Such pellets are encapsulated in a material such as titanium to form an effectively sealed radioactive seed which is useful in certain medical radiological treatments.

25 Claims, 1 Drawing Sheet

PELLET FOR A RADIOACTIVE SEED

BACKGROUND

The present invention relates to a pellet for a radioactive seed used for medical treatments.

Discrete brachytherapy sources have been known to provide an effective method in the medical treatment of diseased tissues. These discrete sources are implanted into a patient at the site of the diseased tissue. To effectively treat the patient, it is desirable to have such a source which will irradiate the diseased tissue while minimizing damage to nearby healthy tissue. Therefore, it is desirable to have a source which will uniformly irradiate an area being treated with a controlled desired dosage of irradiation. Also desirable is a method of accurately detecting the location of the sources after implantation. The usual construction of such sources comprises a radioactive source which is radiopaque by itself or has an X-ray detectable marker disposed therein.

Radioactive iodine sources used in radiation therapy are known and described, for example, in Lawrence U.S. Pat. 3,351,049 and Kubiatowicz U.S. Pat. 4,323,055. The radioactive iodine sources described in those patents generally comprise a container for a carrier body of radioactive material and an X-ray marker. The container is generally made from titanium or stainless steel, thereby providing good mechanical strength of the container with minimum absorption of radiation. An X-ray marker is disposed within the container to permit identification by X-ray photographic techniques of the position and number of seeds.

The carrier body disclosed in the Lawrence patent is constructed of a material such as nylon which will chemically or physically capture the selected radioisotope utilized as a source for radiation and maintain a uniform distribution of the isotope in a fixed bed. A marker material is also disposed within the container for X-ray detection. The patent to Kubiatowicz discloses an X-ray carrier body preferably comprising a silver or silver coated rod. Silver is used because it provides good X-ray detection and because radioactive iodine can be easily attached to the surface thereof by chemical or electroplating processes. However, the interaction of the X-rays from I-125 with the silver produces still lower energy radiations characteristic of silver thus degrading the total I-125 spectrum from the source.

However, it will be appreciated that the prior art fails to recognize a convenient and advantageous method for providing a radioactive iodine source which provides maximum radioactive absorption while being X-ray detectable along its longitudinal axis, and without distorting the characteristic X-ray spectrum of I-125. Also, the prior art fails to recognize a method for easily manufacturing quantities of radioactive sources having a desired controlled radioactivity.

SUMMARY OF THE INVENTION

Accordingly, it is an object of the present invention to provide a new and useful radioactive pellet which overcomes the shortcomings of the prior art.

It is an object of the present invention to provide a radioactive pellet capable of providing desired uniform distribution of radioactivity.

It is another object of the present invention to provide a process for coating a radioactive-absorbing material onto a metal substrate.

It is an object of the present invention to provide a radioactive pellet wherein radioactive material is absorbed by a coating of radioactive-absorbing material in a binder.

It is a further object of the present invention to provide a balanced coating of radioactive-absorbing material, such as carbon, and binder to maximize absorption of radioactive material.

The foregoing objects and others are achieved by providing a radioactive absorption composition comprising a metallic X-ray detectable marker coated with radioactive-absorbing material in a binder wherein radioactive material such as radioactive iodine is absorbed by the radioactive-absorbing material, such as carbon, thereby providing a balance of carbon and binder to maximize radioactive absorption. The X-ray marker preferably comprises tungsten.

BRIEF DESCRIPTION

For a better understanding of the structure, advantages and further features of the radioactive pellets of the present invention, reference is made to the accompanying drawings of various embodiments thereof, wherein.

DETAILED DESCRIPTION OF THE INVENTION

Figure 1:
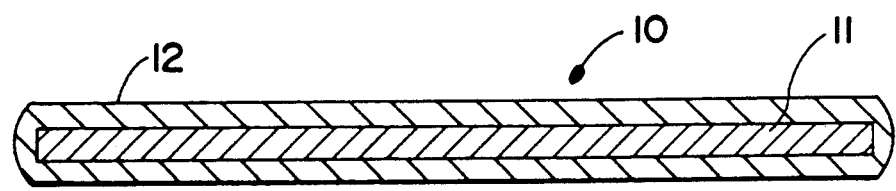
FIG. 1 is a partially schematic cross-sectional view showing a preferred embodiment of the internal structure of the radioactive pellets of the present invention.

A preferred embodiment of the internal structure of the advantageous radioactive pellet of the present invention is illustrated in FIG. 1. The radioactive pellet 10 comprises a metal substrate 11 having a coating 12 thereon. The metal substrate preferably comprises an elongate rod of tungsten or a tungsten alloy. Tungsten is the material of choice because it has mechanical strength which provides a straight substrate on which to coat the carbon and binder. An elongate metal rod made of tungsten imparts stability to the resulting pellet. Furthermore, tungsten is easily detectable by X-ray techniques, and therefore serves as a marker for the radioactive absorption composition. Other materials such as stainless steel or tin may be utilized as the marker, however, tungsten is the most preferred material.

The tungsten rod or marker 11 is coated with radioactive-absorbing material in a binder material. By radioactive-absorbing material we mean any material which will absorb another fluid radioactive material. Such radioactive-absorbing materials may include carbon, activated carbon or charcoal, and ion-exchange resins such as sulfonated polystyrene resins which are available from the Dow Chemical Co. under the name Dowex, methylene-sulfuric phenolic resins, phosphoric polystyrene resins, polystyrene resins containing quaternary ammonium groups, immodiacetic polystyrene resins, and polystyrene resins containing polyamine groups. Other materials may also be used.

A binder material is selected which can readily bond to the substrate and absorb radioactive material without disintegrating or breaking away from the substrate. The binder is preferably water insoluble, so that aqueous solutions of radioactive materials may be used to impregnate the radioactive material into the radioactive-absorbing material. It is believed that the chain length of polymeric binder materials should be long enough to bind the material to the substrate, but also permit the radioactive material to be absorbed therein. Where water-insoluble binders are used, the binder material should have a sufficient number of hydrophillic groups to permit absorption of the radioactive material. Such water insoluble binder materials include cellulose esters such as cellulose acetate, cellulose propionate, cellulose butyrate, and the like. Depending upon the acyl content and hydroxyl content of the cellulose ester, the binding and water absorbing properties of the cellulose ester can be varied. For example, a cellulose acetate presently commercially available has an acetyl content of about 45% (i.e., the percentage of hydroxyl groups in the cellulose which are esterified). When a binder/radioactive absorbing material composition contains about 30% by weight of such a cellulose ester, that binder/radioactive absorbing material layer provides excellent binding and water absorbing properties. Other water insoluble materials such as hydrogenated rosin esters, alkyd resins, silicone resins, polystyrene-olefin copolymers, polystyrene-vinyl toluene copolymers, phenylmethyl silicone resin, phenolformaldehyde resins, and the like may be used. Where such materials may more completely seal the radioactive absorbing material bound therein, that radioactive material may be more preferably primarily located in a substantially discrete layer at or near the outer surface of the layer of binder material.

It will also be appreciated that where the desired radioactive materials are soluble or suspendable in organic solvents, the binder material may be water-soluble but insoluble in such organic solvents, again to preserve the integrity of the binder layer on the substrate during application of the radioactive material. Such water soluble binder materials may include readily available water soluble materials like disaccharides such as sucrose, maltose and the like, polysaccharides such as starch, glycogen and the like, inorganic compositions such as plaster of Paris, calcium sulfate and the like.

As better illustrated in FIG. 3, the radioactive-absorbing material 17 is typically particulate and is dispersed throughout the layer 12 of the binder material. However, the radioactive-absorbing material may, in various embodiments, be located in a more discrete layer at or near the outer surface of the binder material layer 12.

The metallic radiopaque marker rods are coated with binder and radioactive absorbing material, such as carbon and cellulose acetate, in an airborne tumbling process which resembles a fluidized bed system. In one such system tungsten rods are fluidized by blowing a suspension of carbon particles in cellulose acetate dissolved in acetone upwardly through a bed of the rods, thereby substantially uniformly coating the rods with a carbon in cellulose acetate matrix.

It is desirable to have a balance between the radioactive-absorbing material and binder such that radioactive absorption is maximized. In other words, it is desirable to have a sufficient quantity of binder to hold the radioactive-absorbing material on the substrate while having a large amount of the latter material available for absorption of radioactive material. It has been found that about 70% by weight of radioactive absorbing material such as carbon, with about 30% by weight of binder provides a good balance. While the ratio of about 70% radioactive-absorbing material to about 30% binder is preferred, such matrices may be suitable with binder present in amounts in the range of from about 10 to about 50% of the total binder/absorptive material matrix.

The radioactive material to be absorbed into the matrix of the pellet's internal structure is preferably I-125. However, other radioactive materials such as Pd-103, Cs-131, Cs-134, Cs-137, Ag-111, U-235, Au-198, P-32 and C-14, as well as isotopes of rubidium, calcium, barium, scandium, titanium, chromium, manganese, iron, cobalt, nickel, copper, zinc, yttrium, zirconium, indium, cadmium, the rare earths, mercury, lead, americium and neptunium may be used in various applications. The radioactive materials are preferably in fluid or liquid form to facilitate impregnation of the radioactive-absorbing material into the matrix. For example, an aqueous solution of I-125 sodium iodide is preferably used to impregnate a carbon/cellulose acetate coated tungsten rod.

The internal pellets and encapsulated seeds of the present invention are quite small. The metallic rod substrates are typically of a length in the range of about 1 mm to about 10 mm, and of diameter in the range of about 0.1 mm to about 1.0 mm. While circular cross-sectioned rods are preferred, rods having other cross sections may be used. The coating of radioactive-absorbing material and binder is typically of a thickness in the range of about 0.05 mm to about 1.0 mm, and that coating substantially uniformly coats the entire rod, including its ends, as illustrated in FIG. 1. Thus the diameter of the coated internal pellet is in the range of about 0.05 mm to about 3.0 mm. The external capsule which effectively seals the internal pellet to form a useful radioactive seed is typically of a size in the range of about 1.5 mm to about 15 mm in length, with a diameter in the range of about 0.3 to about 4.0 mm. Depending upon the materials used in the pellet and capsule, the total thickness of the capsule wall may be in the range of about 0.05 mm to about 1.0 mm.

For example, substrates having dimensions of about 4 mm in length and about 0.25 mm in diameter are coated with a layer of carbon and binder of approximately 0.1 mm in thickness. The tungsten markers coated by the carbon and binder have final dimensions of about 0.45 mm in diameter and about 4.5 mm in length. Each pellet is thus capable of absorbing I-125 in amounts in excess of about 50 mCi.

In order to obtain the desired radioactivity, the carbon-coated pellets are loaded with a solution of one of the suitable radioactive materials, such as I-125 NaI, at a desired concentration, such as 500 mCi/ml. Each pellet is capable of absorbing a certain amount of liquid. Therefore, only a certain amount of radioactive material can be loaded at one time. If more radioactive material is desired to be absorbed onto the coating, multiple cycles of loading and drying of the pellet may be used. During these cycles of loading and drying, the pellets are allowed to absorb their maximum amount of solution of the radioactive material. Then the pellets are dried briefly, typically with a high intensity lamp. The process of loading and drying is repeated until the desired amount of radioactivity is obtained. Utilizing this method, large batches of radioactive pellets can be manufactured.

While the amount of radioactivity present in each pellet may vary in the range of about 0.1 to about 1000 mCi, most pellets contain about 0.3 to about 100 mCi. Also, the amount of radioactivity per pellet, expressed in mCi, varies depending upon the particular radioisotope being used and the desired application for the pellets.

After the pellets have been loaded with the desired amount of radioactive material, each pellet is encapsulated. Typically, encapsulation is in titanium capsules which effectively seal the pellet. The pellet may be encapsulated in a container made of material other than titanium, provided that the container material does not substantially inhibit irradiation from the seed, and provided that the material is resistant to corrosion by body fluids. Other materials useful for the capsule or container may include stainless steel, platinum, gold, nickel alloy, organic plastic materials such as nylon, silicon, rubber, polyester resin, and fluorinated hydrocarbons, or aluminum and aluminum alloys sealed with an inert overcoating. After the pellets are encapsulated, the actual activity of each seed is monitored by dosimetry. The encapsulated seed can then be implanted into the desired treatment area.

Figure 2:
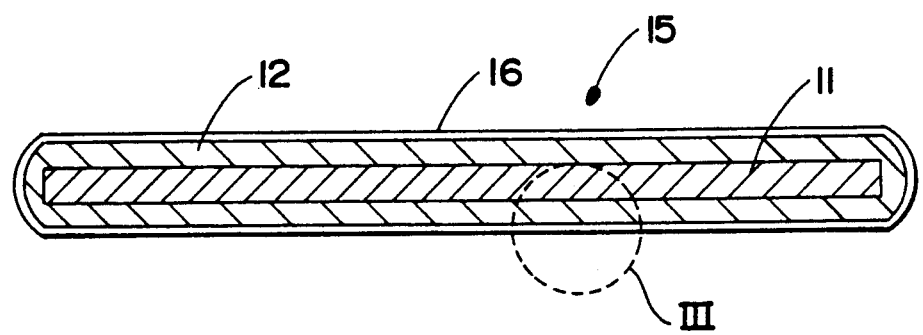
FIG. 2 is a partially schematic longitudinal cross-sectional view of a preferred embodiment of the radioactive seeds of the present invention.
Figure 3:
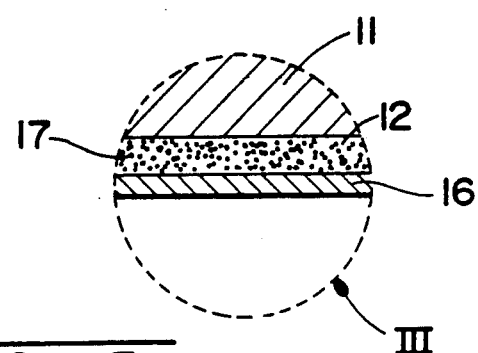
FIG. 3 is a partially schematic enlarged view of a portion of the cross-sectional view of FIG. 2.

A preferred embodiment of the radioactive seeds 15 of the present invention is illustrated in FIG. 2. The seed shown in FIG. 2 is substantially the same as the pellet disclosed in FIG. 1 with the addition that a tubular envelope or capsule 16 is provided around the carbon-coated internal pellet structure. In this embodiment, the tungsten rod is coated with carbon, or other suitable radioactive-absorbing material, and binder, and is further loaded with a radioactive isotope as described above. The pellet internal structure thus obtained is sealed or substantially sealed in a tubular envelope or capsule which is preferably made of titanium. In this embodiment, the coating of activated carbon is of uniform thickness and density, and therefore the irradiation emanating therefrom will be substantially uniform. As with the first preferred embodiment, the pellet thus constituted is loaded with the desired radioactivity, encapsulated preferably by a titanium container, and the resulting radiation of the seed is monitored by dosimetry. Such capsules and encapsulating techniques are further discussed in our copending application Serial No. 07/225,384, filed July 28, 1988, now U.S. Pat. No. 4,891,165.

The methods of making and loading the radioactive pellets of the present invention are further illustrated by reference to the following examples.

EXAMPLE 1

Tungsten marker rods about 4 mm in length and about 0.25 mm in diameter are uniformly coated with about 70% by weight activated charcoal and about 30% by weight cellulose acetate binder, said cellulose acetate having an acetyl content of about 45%, to form a pellet about 0.45 mm in diameter and about 4.5 mm in length. Each pellet is allowed to absorb about 1.0 µl of I-125 NaI solution with a concentration of about 500 mCi/ml. When all of the solution is completely absorbed by each pellet by capilliary action, the pellets are dried under a high intensity lamp. The process of loading and drying is repeated several times depending upon the amount of radioactivity desired in each pellet. Each pellet is then encapsulated in a titanium capsule. The surfaces of the capsules are wiped clean until the removable contamination is reduced to less than 0.005 µCi. The actual radioactivity of the final product is measured using an appropriately calibrated ionization chamber. The final dimensions of the encapsulated seeds are about 0.6 mm in diameter by about 5.0 mm in length.

EXAMPLE 2

A tungsten marker substrate having dimensions of about 4 mm in length and about 0.25 mm in diameter is coated with a layer of carbon and cellulose acetate binder, as in Example 1, approximately 0.1 mm in thickness. The tungsten markers coated by the carbon and binder have final dimensions of about 0.45 mm in diameter and about 4.5 mm in length. The carbon-coated pellets are loaded with a solution of I-125 NaI, at a concentration of 500 mCi/ml. Each pellet is capable of absorbing approximately 1 µl of liquid. Approximately 0.5 mCi of I-125 can be loaded at one time. If more radioactive material is desired to be absorbed onto the carbon coating, multiple cycles of loading and drying of the pellet may be used. With a solution concentration of about 500 mCi/ml I-125, each pellet typically goes through two cycles of loading and drying for each mCi of I-125 loaded. During these cycles of loading and drying, the pellets are allowed to absorb the maximum amount of I-125 solution. Then the pellets are dried briefly, typically with a high intensity lamp. The process of loading and drying is repeated until the desired amount of radioactivity is obtained. The radioactivity of each seed so produced is measured using an appropriately calibrated ionization chamber.

While the foregoing descriptions of the advantageous radioactive pellets and seeds of the present invention have described various embodiments thereof, it will be appreciated by those skilled in the art that various modifications can be made in such radioactive pellets and seeds without departing from the scope or spirit of the invention as stated in the following claims.

What is claimed is:

1. A pellet for a radioactive seed for use in radiation therapy, comprising a metallic rod substrate uniformly and completely coated with binder material having radioactive-absorbing material in the binder material wherein the radioactive-absorbing material is selected from the group consisting of carbon, activated carbon and charcoal.

2. The pellet of claim 1, wherein said binder material is water-insoluble.

3. The pellet of claim 1, wherein said binder material is a cellulose ester.

4. The pellet of claim 1, wherein said binder comprises cellulose acetate.

5. The pellet of claim 1, wherein said binder material is insoluable in organic solvents.

6. The pellet of claim 1, wherein said coating of binder material has a thickness in the range of about 0.05 mm to about 1.0 mm.

7. The pellet of claim 1, wherein the metallic rod substrate comprises a material selected from the group consisting of tungsten, stainless steel, tin, or alloys thereof.

8. The pellet of claim 1, wherein a metallic rod substrate comprises tungsten or an alloy thereof.

9. The pellet of claim 1, wherein the metallic rod substrate has a length in the range of about 1 mm to about 10 mm and a diameter in the range of about 0.1 mm to about 1.0.

10. The pellet of claim 1, wherein the metallic rod substrate has a circular cross-section.

11. The pellet of claim 1, wherein the radioactive-absorbing material is selected from the group consisting of carbon, activated carbon, charcoal, ion exchange resins such as sulfonated polystyrene resins, methylenesulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, and polystyrene resins containing polyamine groups.

12. The pellet of claim 1, wherein the radioactive-absorbing material is particulate and of a particle size in the range of about 1.0 micron to about 100.0 microns.

13. The pellet of claim 1, wherein the radioactive absorbing material is particulate and dispersed throughout the binder material.

14. The pellet of claim 1, wherein the radioactive absorbing material is particulate and is located primarily in a discrete layer at or near the outer surface of the binder layer.

15. The pellet of claim 1, wherein the radioactive-absorbing material comprises an amount in the range of about 10% to about 50% by weight of the total binder/radio- active-absorbing material layer.

16. The pellet of claim 15, wherein the binder comprises about 30% by weight and the radioactive-absorbing material comprises about 70% by weight of the total binder/radioactive-absorbing material layer.

17. The pellet of claim 1, having radioactive material absorbed in the radioactive absorbing material, wherein the radioactive material is selected from the group consisting of I-125, Pd-103, Cs-131, Cs-134, Cs-137, Ag-111, U-235, Au-198, P-32 and C-14, as well as isotopes of rubidium, calcium, barium, scandium, titanium, chromium, manganese, iron, cobalt, nickel, copper, zinc, yttrium, zirconium, indium, cadmium, the rare earths, mercury, lead, americium and neptunium.

18. The pellet of claim 1, having radioactive material absorbed in the radioactive absorbing material, wherein the radioactive material therein is I-125.

19. The pellet of claim 1 having radioactive material absorbed in the radioactive absorbing material, additionally comprising an external capsule covering the exterior of the binder/radioactive-absorbing material layer and substantially sealing the pellet within the capsule, thereby forming a radioactive seed.

20. The radioactive seed of claim 19, wherein said capsule comprises a material selected from the group consisting of titanium, stainless steel, platinum, gold, nickel alloys, nylon, silicon, rubber, polyester resin, chlorinated hydrocarbon resins, aluminum, and aluminum alloys.

21. The radioactive seed of claim 19, wherein the capsule comprises titanium.

22. The radioactive seed of claim 19, wherein the capsule wall thickness is in the range of about 0.05 mm to about 1.0 mm.

23. The radioactive seed of claim 19, wherein the capsule is of a size in the range of about 1.5 mm to about 15 mm in length, and about 0.3 mm to about 4.0 mm in diameter.

24. The radioactive seed of claim 19, wherein the amount of radioactivity present therein is in the range of about 0.1 to about 1000 mCi.

25. The radioactive seed of claim 19, wherein the amount of radioactivity therein is in the range of about 0.3 to about 100 mCi.

* * * * *